United States Patent [19]

Baltes

[11] Patent Number: 4,869,872
[45] Date of Patent: Sep. 26, 1989

[54] PROCESS FOR DRYING AND STERILIZING GOODS IN A CLOSED CIRCULATING SYSTEM

[76] Inventor: Hans Baltes, Heideweg 27, D-4600 Dortmund 30, Fed. Rep. of Germany

[21] Appl. No.: 101,064

[22] Filed: Sep. 25, 1987

[30] Foreign Application Priority Data

Sep. 26, 1986 [DE] Fed. Rep. of Germany ....... 3632820

[51] Int. Cl.⁴ ............................................... A61L 2/00
[52] U.S. Cl. .......................................... 422/1; 34/27; 34/77; 34/196
[58] Field of Search .................. 422/1, 38; 34/12, 27, 34/77, 196

[56] References Cited

U.S. PATENT DOCUMENTS

| 2,074,508 | 3/1937 | Hetzer | 34/77 |
| 2,166,294 | 7/1939 | Hetzer | 34/77 |
| 2,480,227 | 8/1949 | Derr | 422/1 |
| 3,807,948 | 4/1974 | Moore | 68/18 C |
| 3,831,292 | 8/1974 | De Pas | 34/77 |
| 3,958,936 | 5/1976 | Knight, Jr. | 422/1 |
| 4,154,002 | 5/1979 | Moore | 34/27 |
| 4,180,919 | 1/1980 | Baltes | 34/151 |
| 4,519,145 | 5/1985 | Mandel | 34/27 |
| 4,595,560 | 6/1986 | Buchner et al. | 422/38 |
| 4,625,432 | 12/1986 | Baltes | 34/196 |

FOREIGN PATENT DOCUMENTS

| 3343236 | 6/1985 | Fed. Rep. of Germany . | |
| 0372773 | 4/1973 | U.S.S.R. | 422/1 |

Primary Examiner—David L. Lacey
Assistant Examiner—V. Manoharan
Attorney, Agent, or Firm—Felfe & Lynch

[57] ABSTRACT

A process for drying and sterilizing items, such as laundry articles, bed clothing, leather goods, hair care instruments, medical instruments, etc., in a cabinet having an internal air circuit and an external air circuit which are in contact with one another through a condensation and refrigeration unit thereby permitting drying of an article at a warm air temperature not exceeding 100° C. followed immediately by sterilization of the article in a temperature range of 121° C. to 135° C.

12 Claims, 3 Drawing Sheets

PROCESS FOR DRYING AND STERILIZING GOODS IN A CLOSED CIRCULATING SYSTEM

FIELD OF THE INVENTION

The invention relates to a process and an apparatus for drying and sterilizing materials such as laundry items, very sensitive fabrics, pure wool, bed linens, pillows, down comforters, wool blankets and leather and other articles, such as tableware, medical instruments, combs, scissors, brushes, knives and shavers, etc. in a drying and sterilizing tank which performs both steps in the same treatment chamber. Specifically, the items are first dried in an upright or hanging position without being mechanically moved and the sterilization step is performed immediately after the drying step in the same chamber.

BACKGROUND OF THE INVENTION

Various methods are known for drying and sterilizing goods. Tumble dryers of a wide variety are able to dry fabrics at different temperatures. In such a case the constant movement of the goods is combined with the input of heated air. In addition to these tumble dryers there are also dryers in which the hanging goods are exposed to air which is either warmed or is at room temperature.

The sterilization of the laundry itself is not normally performed in the dryers, and additional procedures are necessary for this purpose. For example, various sterilization processes are known in the field of hygiene and microbiology; the methods relevant to the sterilization of laundry are discussed below.

Autoclaving at 121° C. and 2 bar steam pressure is a widely used technique for disinfecting temperature-sensitive materials. This process is used primarily when the material cannot be expected to withstand temperatures of 160° C. or more without damage.

Other means of sterilizing such heat-sensitive items, include exposing the goods to gases such as ethylene oxide, formaldehyde, chlorine, ozone, etc. The goods can also be disinfected in an aqueous medium with disinfectants containing, for example, oxidants or aldehyde groups (formaldehyde). Although these chemical processes can be effective. They are also very time-consuming.

Further, the sterilization of very delicate goods may be accomplished with irradiation with gamma rays; x-radiation cannot be used with a sufficient dosage rate to achieve sterilization.

With the modern-day method of laundering items at 30°, 60° and 90° C. it must basically be assumed that boiling the laundry is no longer practiced. Furthermore, many kinds of fabric are so delicate that washing at higher temperatures would be harmful to the materials. In all of today's washing methods, moreover, severe mechanical stresses are involved which also limit the level of the washing temperature. For the same reasons, tumble dryers for delicate goods cannot use temperatures higher than about 50° to 60° C., since otherwise the thermal and mechanical stresses would soon cause permanent damage.

From this it is apparent that, in today's washing processes followed by drying in tumble dryers, cleaning is quite possible, but subsequent sterilization of the laundry is not feasible. It must therefore be assumed that the dry laundry afterward is still infected with a load of germs.

Consequently, there is a need for subjecting laundered goods, articles of clothing, etc. to sterilization. Since fabrics are damaged at high temperatures such as 160° C., the goods must be sterilized by autoclaving, by chemical substances, or by radiation.

Operating an autoclave requires technical skill and can be considerably dangerous to an untrained lay person. Both high temperatures, e.g., 121° C., so that some parts of the apparatus are at that temperature, and a pressure of 2 bar must be built up, which calls for a pressure chamber which must have a complex opening system for equalizing the chamber and exterior pressures. An autoclave furthermore requires technical maintenance which considerably increases the cost of operating this system.

Articles of clothing are also sterilized by chemical methods such as those discussed above. It should be noted that some of the chemical substances involved can have negative effects on the skin of the wearer, because unless they are completely removed from the fabrics at the end of the sterilization process, substances of high molecular weight can remain in the goods and afterward produce defensive reactions in the wearers such as allergies, for example. Yet these chemical substances cause difficulties not just for the wearer but also in their removal. If gases are involved, they are often released into the atmosphere, and if liquids are involved they pollute the waste water which is released into the environment. Both contamination of the air and of the ground water must be avoided at all costs.

Even sterilization with gamma rays poses a certain problem: the germs are killed by this treatment without heating the goods or exposing them to chemicals, but it must be noted that such a dose of radiation cannot be achieved by an x-ray apparatus but only by natural radionucleotides. Consequently, the problem of installation costs is aggravated by the problem of disposal.

The invention is addressed to the problem of performing drying and sterilizing in a relatively simple manner, while at the same time minimizing the drying and sterilization time, keeping the costs reasonable, avoiding environmentally harmful gaseous or water-soluble substances, rendering the operation safe, simple and easy for technically untrained users, and moving the air with which the goods come in contact in the drying and sterilization processes within a closed circuit so that contamination of the environment will be impossible.

SUMMARY OF THE INVENTION

The object of the invention is to address the problems discussed above and others which will become apparent to those skilled in the art by the steps of the inventive process involving carrying an air stream in both an inner circuit and an outer circuit contacting both circuits with one another through a condensation and refrigeration unit to form a condensation, shutting off the condensation unit after the drying step has ended, and cooling the condensation and refrigeration unit after the sterilization process is completed. During the drying and sterilization steps the condensation may be performed at a warm air temperature under 100° C., preferably at 45° to 60° C., and the sterilization step is carried out at a hot air temperature in the range of between 121° and 130° C., preferably between 125° and 130° C.

The inventive apparatus is a cabinet having inner walls which define an interior chamber, a closed internal air circuit means, a condensation and refrigeration unit, an external air circuit means and internal and external blowers associated with each of the inner and external air circuit means, respectively. The internal air circuit means is a channel defined between the inner and outer walls of the cabinet through which air flows into the interior chamber through openings in the inner walls and out of the chamber into the condensation and refrigeration unit which removes its moisture. During the drying phase, air is also circulated in the external circuit means through the condenser unit and out of the apparatus by means of the external blower.

For the person skilled in the art, it is completely unexpected that a complete sterilization is possible at temperatures that are used according to the invention. That sterilization is practicable at these temperatures is even in contradiction to the state of the art, since it is considered proven that dry sterilization is possible only at temperatures of 160° C. or more.

BRIEF DESCRIPTION OF THE DRAWINGS

A preferred embodiment of the invention is illustrated in the accompanying drawings as follows.

DETAILED DESCRIPTION OF A PREFERRED EMBODIMENT

Figure 1:
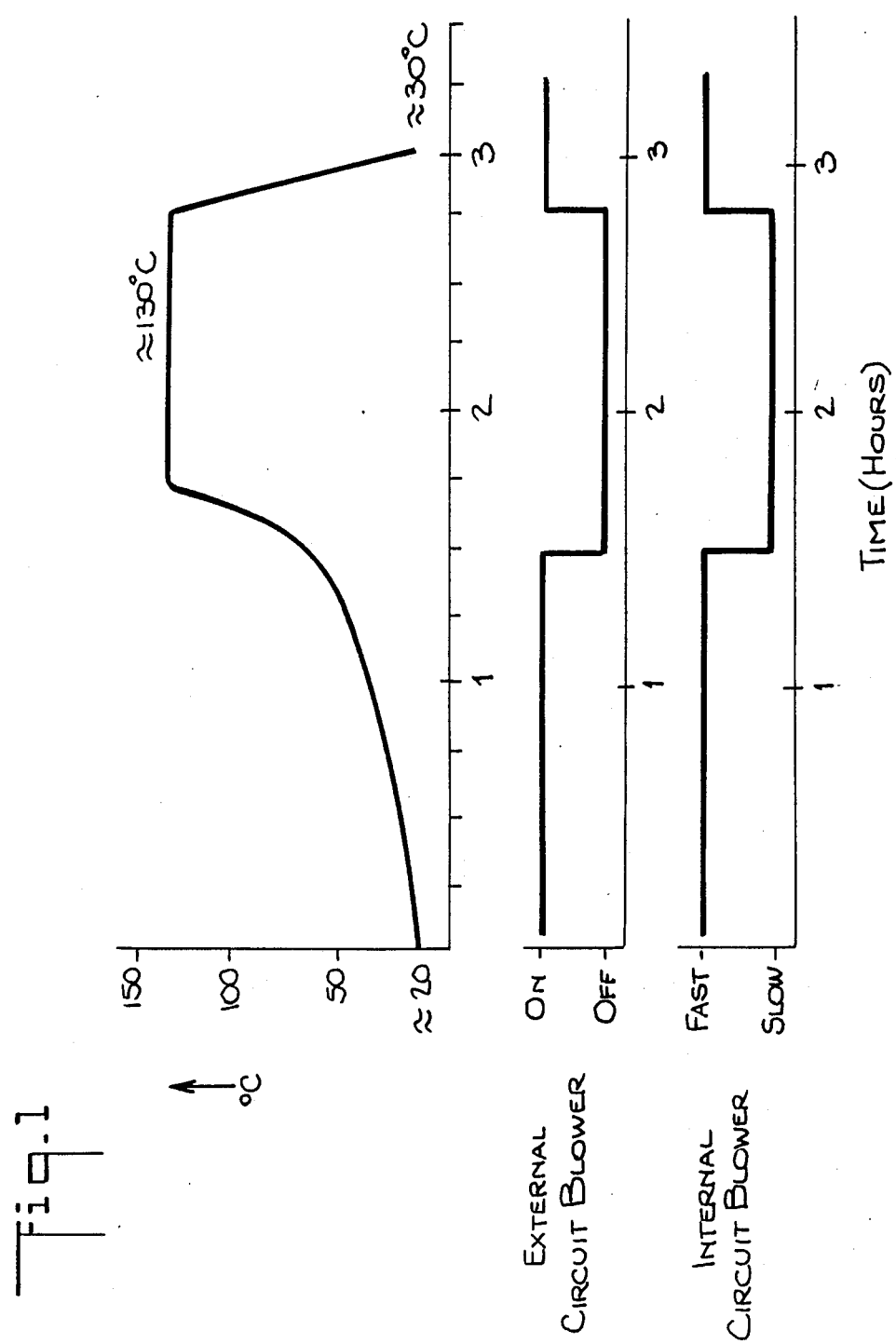
FIG. 1 are graphs illustrating a relational temperature to time curve accomplished in the inventive machine and in the internal and external circuits of the invention.

FIG. 1 is a graph showing the inventive process by way of an example. The goods are at room temperature when placed into the drying and sterilizing machine and are dried within 1½ hours, the temperature rising gradually to about 65° C. The moisture flows from the goods into the inner air circuit and is removed from the air circuit by means of the condensation and refrigeration unit. When the air moisture content amounts to about 65%, or when at least 35% of the moisture has been removed from the goods, the machine changes over so that the inner air stream continues to move but more slowly that is, at a reduced velocity, while the outer cooling circuit is completely shut off. The inner temperature thus increases to about 125° to 130° C.; this happens in about 15 minutes Not until then does the actual sterilization phase take place. It runs for more than one hour. During this period of time the temperature is kept constant within the enclosure by a regulating circuit consisting of temperature sensors in contact with the inner chamber, a device for establishing the required temperature, and a heating element that can be turned on and off. Due to the air circulation that takes place during the sterilization, the assurance is provided, in the case of the heating element which is situated outside of the inner wall but inside of the inner air stream, that it will react to correct minor temperature fluctuations in the interior.

After the sterilization step the sterile goods are cooled down again. This is accomplished by the fact that the internal air stream again runs at full power and the external cooling is likewise turned on again. Thus, within a short time, it is possible to reduce the temperature by about 90° to 100° C. The goods and the inner parts of the cabinet are at about 30°–40° C. after this cooling phase, so that they constitute no hazard for the operating personnel. After this process the drying and sterilizing machine is completely ready to be used again.

Figure 2:
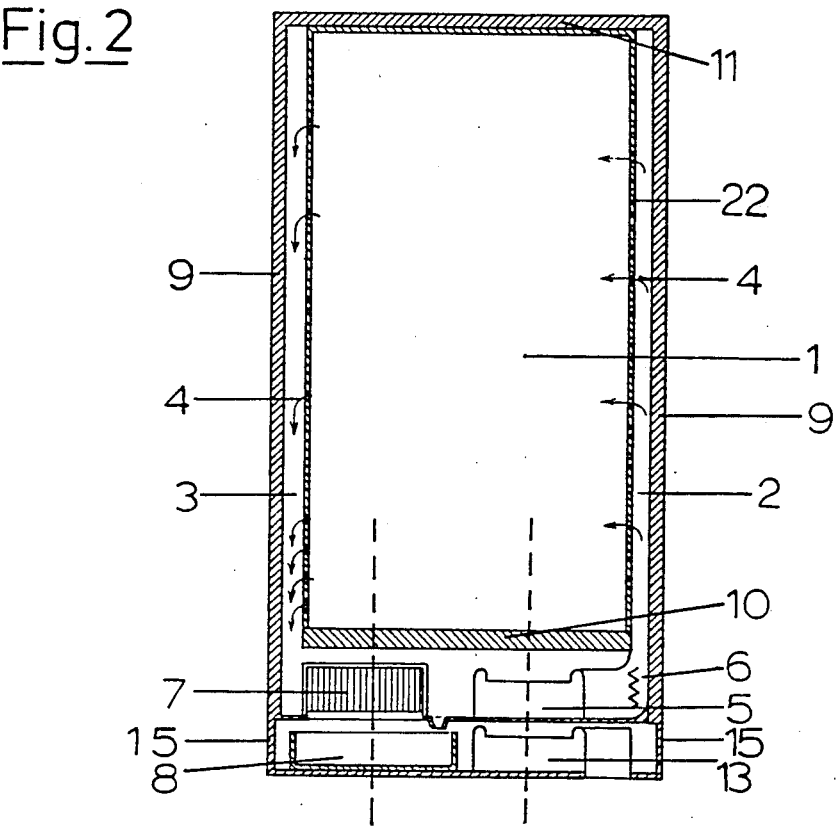
FIG. 2 is a front side elevational view in cross section of the drying and sterilizing appliance according to the invention.
Figure 3:
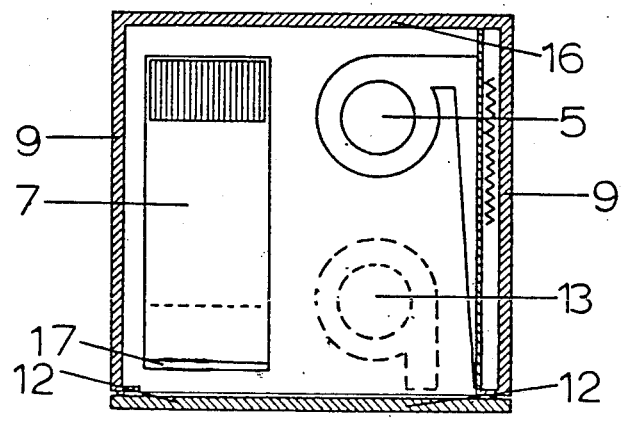
FIG. 3 shows a top plan view in cross section of the bottom part of the inventive drying and sterilizing appliance illustrating the blowers and the condensation and refrigeration unit.
Figure 4:
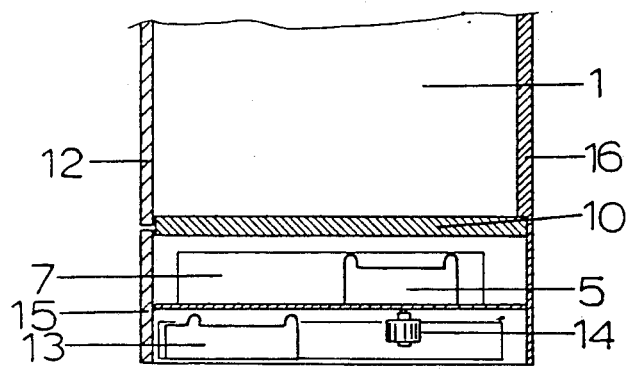
FIG. 4 is a side elevational view in cross section of the drying and sterilizing appliance taken along the lines C–D of FIG. 2.

FIG. 2 shows a drying and sterilizing machine in cross section as seen from the front. An interior chamber 1 has on inner side walls 22 openings 4 through which air can both enter the chamber 1 and leave it. The air enters the chamber through an air intake duct 2 and leaves the chamber through the openings 4, passing through an air discharge duct 3 to a condensation and refrigeration unit 7. After passing through the condensation and refrigeration unit 7 the air stream is aspirated by a radial internal blower 5 for its internal circulation in the invention and then the airstream is carried past heating elements 6 to complete the circuit of the inner system. The inner air system thus provides a closed circuit. Under the condensation unit and refrigeration unit 7 there is a drip pan 8; the two are in communication through a drain opening 17 as illustrated in FIG. 3.

To assure good thermal insulation, the inner side walls 22 may be thermally insulated. Additionally, the outer side walls 9, the back wall 16, the door 12, the cover 11 and the inner bottom 10 may be thermally insulated as well. The material must, however, be insensitive to a change in the humidity of the air. With a view to use in a drying and sterilizing machine it is necessary that the inside walls not be damaged by a rapid change from moist heat to extreme dryness.

A thermal insulating material furthermore guarantees that the fabrics being sterilized will not yellow, especially at points of contact between textiles and inner walls of the cabinet or frame. In the case of some delicate textiles it is not possible to reliably prevent such yellowing upon contact with metal surfaces and metal walls.

Such thermal insulating material furthermore prevents the operating personnel from suffering burns if, after opening the cabinet during the sterilization phase, their bare hands come accidentally in contact with the inner surfaces of the drying and sterilizing cabinet. Furthermore, this insulating material has the great advantage that, due to the low absorption of heat and the extreme thermal insulation, the heating and cooling phase can take place quickly and with little expenditure of energy.

If in addition to the inner walls 22 the outer walls 9 of the drying and sterilizing machine are made up of an insulating material, good insulation from the environment is also assured. The advantage of such a cabinet is that good insulation is made possible between the high heat of the interior and the ambient temperature. As a result, energy can be saved during warm-up, the cooling phase takes place rapidly, and complicated and bulky shielding from surrounding furniture and walls is unnecessary. Such a cabinet could thus be placed directly against another appliance or against a wall without the need for an air space to dissipate the heat and for insulation.

Figure 6:
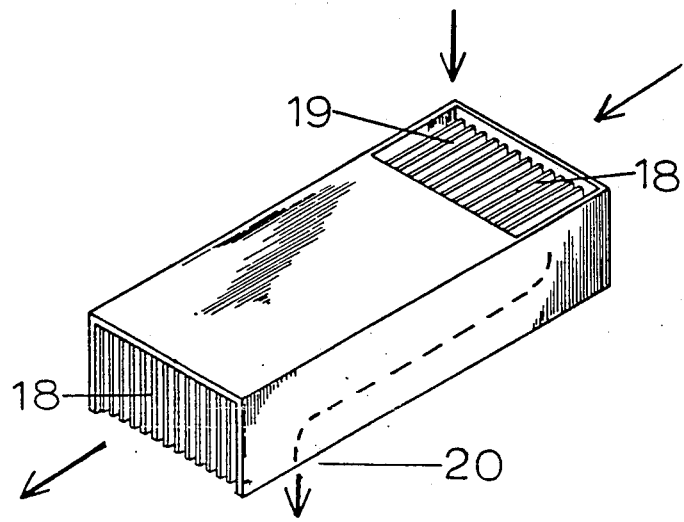
FIG. 6 is a perspective view of the condensation and refrigeration unit of the invention.

In order to cool the condensation and refrigeration unit 7 properly, air is aspirated from the exterior into the external, open circuit, and is drawn through the condensation and refrigeration unit 7. The air is taken over by a radial blower 13 for the external circuit, and ejected from the cabinet again by the blower 13. As illustrated in FIG. 6, the exterior cold air is aspirated through an inlet opening 19 into the condensation and refrigeration unit 7, carried past the fins 18 of the condensation and refrigeration unit 7, and leaves this unit at an outlet 20 from the condenser. Since the condensation and refrigeration unit 7 operates as a counter-flow condenser, the cold outside air is heated as it passes through the fins 18.

To accelerate the cooling, another possibility is to draw some of the cooling air over the outside walls 9 (e.g., ducts in the side walls, cover 11 and/or back wall) in order to cool them.

To prevent overheating of a motor 14 which drives the radial blower 5 for the internal circuit, this motor 14 is situated outside of the internal circuit.

Figure 5:
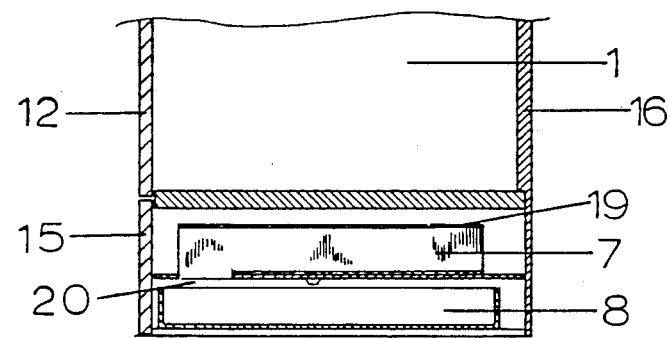
FIG. 5 is a side elevational view in cross section of the drying and sterilizing machine taken along the lines A–B of FIG. 2.

All units, i.e., the radial blowers 5 and 13, the condensation and refrigeration unit 7 and the drip pan 8 are situated in a base 15, which can be seen in FIGS. 2 and 5, both in a side view and in a top view.

It is also possible, of course, to place a part of all of the arrangements in the top part of the cabinet, if this is desired.

Generally, fabrics are not exposed to temperatures around 125° to 130° C. but operating at these temperatures is possible since a number of conditions are fulfilled in the inventive process. For one thing, the drying phase is performed at preferably 40° to 65° C., and for another the fabric is not subjected to mechanical stress during the hot phase of 121° to 130° C.

By this invention a number of advantages over the former state of the art are achieved.

Thus, all fabrics such as blends of fabrics, cotton, pure wool, pure silk, pure synthetics and pure viscose are both gently dried and sterilized. Furthermore, it is possible to subject leather, leather shoes, or even featherbeds to the inventive process, which is a great contribution to hygiene in these areas. In the drying process a very gentle process is used, since the moisture is not boiled away but evaporated, i.e., the drying takes place below the boiling temperature of water, at standard pressure.

The goods may be dried while they are hanging in the drying and sterilizing cabinet so that, in contrast to tumble dryers, there is no wear, no wrinkling and no crushing of the goods. No matting, no tangling, no discoloring and no shrinkage occur so that ultimately the clothes last longer and save the user money.

After drying, the goods are smooth, so that further treatment is hardly necessary, which also results in a reduction of costs.

In contrast to tumble dryers, this apparatus needs less space. Since there is no mechanism comparable to the tumble dryer, installation is also much less problematical. Since only blowers involve mechanical movement, the nuisance of propagating noise, for example, through the walls or the floors housing the dryers, is avoided.

Since there is no danger of fire in the apparatus, it can also be operated without supervision. Since the machine according to the invention is made of parts which are highly technically developed, a high degree of reliability is achieved, so that the apparatus is very useful to both the hospital sector and the hotel business. In the case of hospitals and clinics, this drying and sterilizing machine offers a good possibility for sterilizing hospital uniforms, medical instruments, tableware and dishes, plus handkerchiefs, bedding and clothing. There is no longer any need to resort to more expensive apparatus or to chemical substances which sometimes accomplish little more than disinfection, and which furthermore also seriously pollute the environment. Instead it becomes possible to sterilize goods in a technically simple manner. Such an appliance is bound to be of great interest to hospitals if only because some infections are spread precisely by hospital personnel, and can lead to so-called "hospitalism". To combat these germs with drugs or chemicals is considered quite problematical, because the germs are characterized by a stubborn resistance to these treatments. Nevertheless they are sensitive to sterilization by temperature.

Another use of the inventive device is in the field of hair care. The inventive device and method may be used by hairdressers and barbers to sterilize combs, scissors, brushes, knives and razors.

Sterilization Test Results with Sample Germs

In order to prove that sterilization has actually been accomplished, a variety of germ tests were performed. For this purpose, material contaminated with germs, such as bacteria and yeast, were placed in various locations in the drying and sterilizing cabinet of the invention. The test germs used were *Staphilococcus aureus, Pseudomonas aeruginosa, Bacillus subtilis* and *Candida albicans*. These germs are widespread in occurrence and, with the exception of *Bacillus subtilis*, all problematically occur in hospitals since they are difficult to combat because of their resistance to antibiotics. These germs were cultivated in a complete nutrient medium and applied in a high concentration to a test fabric. At the same time the germs were also cultivated in blood and the two mediums were mixed together. This mixture, i.e., the complete medium and the blood medium, generally provides a protective range for the germs which permits them to withstand extreme environmental conditions.

In the inventive cabinet the contaminated material was exposed to an actual temperature of 125° to 130° C. Then the material was exposed under sterile conditions to the complete medium which had been sterilized. The longest incubation time for any of the tested germs amounts to 8 days at 36° C., so that even one surviving germ suffices to permit definite growth which would be detected in the culture medium. The results of this test series show that an effective sterilization time of 30 minutes is sufficient to destroy all germs which do not form endospores. For the successful sterilization of even these endospore formers, 120 minutes of sterilization time is sufficient to destroy them. With an apparatus according to the invention it is therefore possible to achieve secure sterilization if the goods are exposed to this temperature for 120 minutes at temperatures between 125° and 130° C.

Such conditions were not achievable in the apparatus known in the art prior to the present invention.

Germs which are on the fabric being dried in the inventive drying and sterilizing cabinet must not be released to the environment. This problem is solved by a closed, internal circuit.

It will be understood that the specification and examples are illustrative but not limitative of the present invention in that other embodiments within the spirit and scope of the invention will suggest themselves to those skilled in the art.

What is claimed is:

1. A process for drying and sterilizing items in a drying and sterilizing chamber comprising:
   (a) inserting an item for sterilization into a drying and sterilization chamber -having an internal air circuit means, an external air circuit means and a condensation and refrigeration means;
   (b) circulating a first air stream through said internal circuit means and said chamber;
   (c) circulating a second air stream through said external air circuit means and said condensation and refrigeration means so that said first air stream and said second air stream come in contact with each other;
   (d) heating said first air stream to a warm temperature value of at least 40° C.;
   (e) drying said item in said chamber so that moisture is removed from said item by said first air stream;
   (f) condensing the moisture from said first air stream by the condensation and refrigeration means;
   (g) turning off the circulation of the second air stream in said external air circuit means;
   (h) increasing the temperature of the first air stream to a hot temperature having a value higher than 121° C.;
   (i) sterilizing said item in said chamber in said first air stream at said hot temperature;
   (j) cooling said first air stream to a temperature value lower than said warm temperature value and circulating said second air stream through said external air circuit means; and
   (k) removing said item which has been sterilized from said chamber.

2. The process according to claim 1 wherein said warm temperature value is in a range of about 40° C. to 100° C.

3. The process according to claim 2 wherein said warm temperature value is in a range of about 40° C. to 60° C.

4. The process according to claim 1 wherein said hot temperature value is in a range of between 121° C. to 130° C.

5. The process according to claim 4, wherein said hot temperature value is in a range of about 125° C. to 130° C.

6. The process according to claim 1 wherein said turning off of the second air stream in the external air circuit means step further comprises reducing a velocity of the first air stream of said internal air circuit means.

7. The process according to claim 1 wherein said drying step further comprises removing at least 35% of the moisture from the item in said chamber.

8. The process according to claim 7 wherein removing the at least 35% of the moisture of the item causes the circulation of the second air stream in said external air circuit means to be turned off.

9. The process according to claim 1 wherein inserting said item of step (a) is accomplished by hanging said item in said chamber.

10. The process according to claim 1 wherein, said chamber of step (a) lacks mechanically moving parts to mechanically move the item inserted into it about the chamber.

11. The process according to claim 1 wherein said internal air circuit means is a closed system and said external air circuit means is an open system.

12. The process according to claim 1 wherein said inserted into said chamber is selected from the group consisting of a laundry article, bed clothing, a leather-good, a medical instrument, a hair care instrument, tableware, a natural fabric material, a synthetic fabric material, and a mixture thereof.

* * * * *